United States Patent [19]

Dell et al.

[11] Patent Number: 4,594,357
[45] Date of Patent: Jun. 10, 1986

[54] DEPOT ANTIINFLAMMATORY AGENTS

[75] Inventors: Hans-Dieter Dell, Berg.-Gladbach; Bernhard Pelster, St. Augustin; Reinhold Kraüs, Cologne; Detlef Schierstedt, St. Augustin, all of Fed. Rep. of Germany

[73] Assignee: Troponwerke GmbH & Co., Cologne, Fed. Rep. of Germany

[21] Appl. No.: 622,425

[22] Filed: Jun. 20, 1984

[30] Foreign Application Priority Data

Jul. 5, 1983 [DE] Fed. Rep. of Germany ....... 3324192

[51] Int. Cl.$^4$ .................. A61K 31/19; A61K 31/24
[52] U.S. Cl. .................................. 514/537; 514/538; 514/561
[58] Field of Search ................. 424/317, 319, 309; 514/537

[56] References Cited

U.S. PATENT DOCUMENTS

| | | | |
|---|---|---|---|
| 3,590,039 | 6/1971 | Sallman et al. | 424/319 |
| 3,673,243 | 6/1972 | Yamamoto et al. | 424/319 |
| 3,678,094 | 7/1972 | Shen et al. | 424/319 |
| 3,778,470 | 12/1973 | Sallman et al. | 424/319 |
| 4,307,113 | 12/1981 | Anderson | 424/319 |

OTHER PUBLICATIONS

Analgetics, De Stevens, Medicinal Chem. A Series of Monographs (1965), pp. 436–437.

*Primary Examiner*—Stanley J. Friedman
*Attorney, Agent, or Firm*—Sprung, Horn, Kramer & Woods

[57] ABSTRACT

The invention relates to depot formulations containing, as an active antiinflammatory and/or analgesic agent a compound of Formula I, infra together with a suspension medium. Typical suspension agents are glycerides and/or esters of mono- or poly-hydric alcohols as well as selected ethers, alcohols and amides.

11 Claims, No Drawings

DEPOT ANTIINFLAMMATORY AGENTS

The present invention relates to depot formulations containing a compound of the formula I

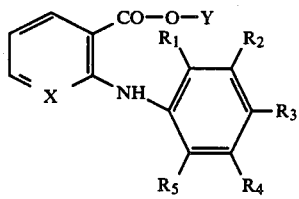

in which
R$_1$–R$_5$ represents hydrogen, halogen, alkyl or substituted alkyl,
X represents N or CH and
Y represents H, metal ions, alkyl or substituted alkyl.

Antiinflammatory-analgesic active compounds have hitherto been used in medicine by the oral, rectal, cutaneous and intramuscular mode of administration. The biological half-life and the duration of action here is decisive for the administration plan. Daily multiple administrations must be effected for many of these medicaments.

To prolong the duration of action, numerous active compounds in special galenical processing as retard products have been described, for example 1-(p-chlorobenzoyl)-5-methoxy-2-methylindole-3-acetic acid, as a sustained release product, in U.S. Pat. No. 4,173,626.

As yet, there is no antiinflammatory agent/analgesic in depot form which still displays an adequate action when administered at intervals of several days.

The object of the present invention was thus to provide an antiinflammatory agent/analgesic in depot form.

The invention is based on the fact that, surprisingly, it has been found that compounds of the formula I have a powerful inflammation-inhibiting action, when used intramuscularly in a suitable form, for a substantially longer period than the same active compounds in, for example, a form to be administered orally.

The present invention thus relates to agents containing at least one compound of the formula I and a suspension medium, and to a process for the preparation of these agents and the use of these agents as a depot antiinflammatory agent or a depot analgesic.

The depot formulations contain at least one of the compounds of the formula I and a suspension medium. In the context of the present invention, suspension medium is understood as meaning: triglycerides with mono- and dicarboxylic acids of C$_6$–C$_{20}$ chain lengths, in saturated or unsaturated, and optionally also hydroxylated form (in particular oily triglycerides, such as viscoleo, cottonseed oil, groundnut oil, maize germ oil, almond oil, olive oil, castor oil and sesame oil). Esters of monohydric or dihydric alcohols, for example propylene glycol, butanediols and higher alkanols and alkanediols of C$_2$–C$_{24}$ chain lengths, with the abovementioned acid components are also suitable (examples which may be mentioned are: ethyl oleate, isopropyl myristate and isopropyl stearate) and furthermore benzyl benzoate and glycofurole.

The suspension medium can also contain alcohols and amides (saturated or unsaturated, aliphatic or aromatic), instead of or besides suitable esters, and the amides can also be cyclised, for example pyrrolid-2-one (as the monomer or polymer) which are toxicologically inert.

The content of suspension medium in the depot formulation according to the invention is between 2 and 90%, preferably 3 and 70% and particularly preferably 10 60% by weight.

The sterile solutions or suspensions for injection purposes can additionally contain gelling agents, for example aluminium stearate, in order to delay release from the oil depot.

If appropriate, one or more preservatives, for example benzyl alcohol, phenyl ethyl alcohol, chlorobutanol and cholesterol can be used. If approprate, one or more antioxidants, for example tocopherols, nordihydroguaiaretic acid, anisole derivatives, i.e. 2- and 3-tert.butyl-4-hydroxy-anisole, ascorbic acid esters, i.e. ascorbylpalmitat, propyl, octyl, dodecyl-gallate, gallic acid esters and butylhydroxytoluenes, are added to the suspension medium.

If appropriate, the depot product can also initially be in a separated form (active compound/dissolving or suspension medium) and be combined before use (for example dry ampoules).

According to the invention, a compound of the formula I is understood as meaning:

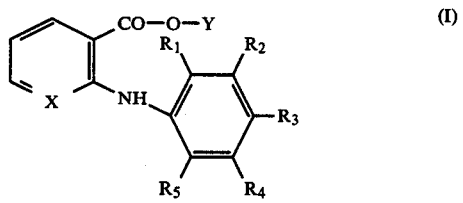

in which
R$_1$–R$_5$ represents hydrogen, halogen, alkyl or substituted alkyl,
X represents nitrogen or CH and
Y represents hydrogen, metal ions, alkyl or substituted alkyl.

R$_1$–R$_5$ and Y as alkyl denote groups with preferably 1–6 C atoms; substituted alkyl is hydroxyalkyl, alkoxyalkyl, halogen denotes especially fluorine, chlorine or bromine, preferably chlorine. Metal ions are understood as meaning ions of alkali metals, alkaline earth metals or aluminium.

Preferred compounds of the formula I are understood as meaning those
in which:
R$_1$–R$_5$ represents hydrogen, alkyl with 1 to 4 C atoms or trihalogenoalkyl,
X represents nitrogen or a CH group and
Y represents hydrogen, metal ions, alkyl with 1–4 C atoms, alkoxy, alkoxyalkyl, hydroxyalkyl, hydroxyalkoxyalkyl or trihalogenoalkyl, the number of C atoms in each case being between 1 and 6 and more specifically for the alkyl chain to have 1 to 4 C atoms and to be straight-chain or branched.

Particularly preferred compounds of the formula I are to be understood as meaning those in which
R$_3$ and R$_4$ represents hydrogen,
R$_1$, R$_2$ and R$_5$ represents methyl, trifluoromethyl or chlorine,
X represents a CH group and Y represents hydrogen, metal ions, alkyl with 1 to 4 C atoms or by substituted alkyl.

Very particularly preferred depot formulations according to the invention are understood as meaning those which contain, as the active compound, at least one of the following compounds:

1. N—(α,α,α-Trifluoro-m-tolyl)-anthranilic acid

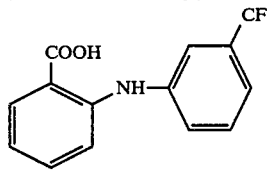

2. N—(2,3-Xylyl)-anthranilic acid

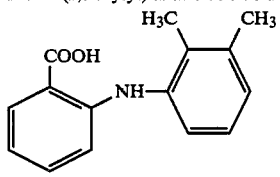

3. N—(2,6-Dichloro-m-tolyl)-anthranilic acid

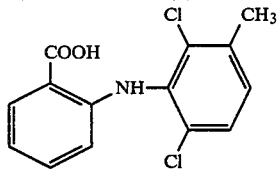

4. N—(3-Chloro-o-tolyl)-anthranilic acid

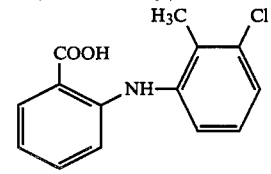

5. N—(2,3-Dichlorophenyl)-anthranilic acid

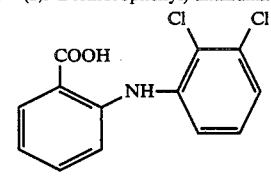

6. 2-(α,α,α-Trifluoro-m-toluidino)-nicotinic acid

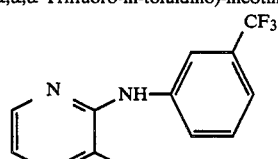

7. 2-(2,3-Xylidino)-nicotinic acid

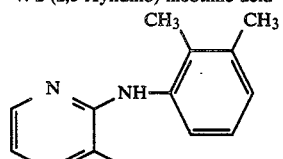

8. 2-(2-Methyl-3-trifluoromethylanilino)-nicotinic acid

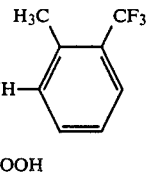

9. 2-(3-Chloro-o-toluidino)-nicotinic acid

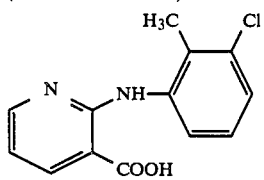

10. 2-(2,6-Xylidino)-nicotinic acid

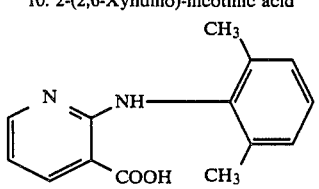

and salts, esters etc. thereof, in particular 11. 2-(2-Hydroxyethoxy)-ethyl N—(α,α,α-trifluoro-m-toluene)-anthranilate

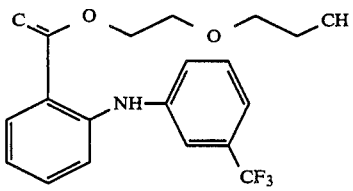

12. Ethoxymethyl N—(2,6-dichloro-m-tolyl)-anthranilate

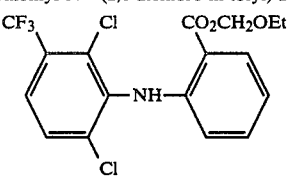

13. Butyl-N—(α,α,α-trifluoro-m-tolyl)-anthranilate

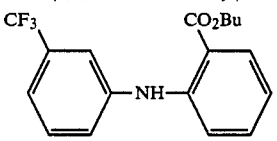

14. Ethyl N—(α,α,α-trifluoro-m-tolyl)-anthranilate

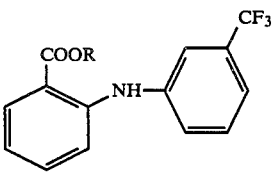

a: R = ethyl

15. Isopropyl N—(α,α,α-trifluoro-m-tolyl)-anthranilate

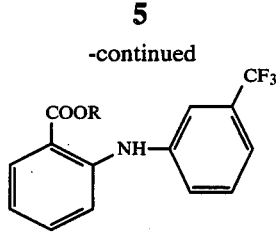

b: R = iso-propyl the methyl, ethyl, i- and n-propyl, i-, n- and tert.-butyl, prophyl and hexyl esters of this acid and corresponding hydroxyalkyl esters and hydroxyalkoxyalkyl esters with 1 to 4 C-atoms between the oxygen atoms.

The depot agents according to the invention contain the pharmacologically active compounds of the formula I in amounts of 3 to 80% by weight, preferably 5 to 75% by weight and particularly preferably 10 to 70% by weight.

The depot agents very particularly preferably contain, as the suspension medium, at least one from the group: viscoleo, isopropyl myristate, ethyl oleate, castor oil, sesame oil, arachis oil, cottonseed oil, almond oil, olive oil, neat's -foot oil, neutral oil and maize oil.

Viscoleo is understood as meaning a mixture of triglycerides of saturated fatty acids of medium chain length, which is neutral and is liquid at room temperature. In particular, viscoleo is understood as a mixture of triglycerides of saturated fatty acids, in which the acids are: caprylic acid (45–60%, caprinic acid (35–50%) and laurinic acid (2–10%).

Neat's-foot oil is understood as the pale yellow-coloured oil with only a slight odour which is obtained from the hooves of cattle and sheep or from the feet of horses by boiling up with water, neutral oil, for example. Miglyol, is caprylic/capric acid triglyceride, which is a liquid of low viscosity.

Besides the active compounds of the formula I, the depot agents according to the invention can also contain other pharmaceutical active compounds.

The formulations described above are prepared by intensive mixing of the active compound or active compounds of the formula I with the suspension medium in the abovementioned proportions.

Solutions are usually prepared by dissolving the active compounds and auxiliaries, which have a low germ content or are sterile, in the sterilised solvent. The solution is then subjected to sterile filtration and filled into ampoules.

The suspension is prepared from sterile active compounds and auxiliaries under aseptic conditions. If appropriate (both with the solution and the suspension), the procedure is carried out under an inert gas, and heat-sterilisation is possible in particular cases.

The amount contained in the ampoules is 0.5–5.0 ml. The solution or suspension to be administered is preferably 1–3 ml, and particularly preferably 1–2 ml.

The oedema-inhibiting and analgesic action of the test substances following intramuscular administration of an appropriate depot formulation was determined with the aid of oedema of the rat paw induced by carrageenan or by means of the Randall-Selitto test [Arch. int. Pharmacodyn. 111, 409 (1957)].

The experiments were carried out on male rats [strain: Bor: WISW (SPF-Cpb), weight about 200 g]. A depot product was administered once intramuscularly to the animals and the antiinflammatory action on the following days was tested by inducing carrageenan oedema. In each case three groups or 5 animals each were investigated per day, the first group consisting of 5 untreated animals, the 2nd group of 5 animals treated only with solvent (for example viscoleo) and the 3rd group of 5 animals treated with depot product (for example 2-(2-hydroxyethoxy)-ethyl-N-(α,α,α-trifluoro-m-tolyl)anthranilate (formula 11) in viscoleo).

The paw volumes were measured by the method of F. Kemper and G. Ameln [Z. ges. exp. Med. 131, 407 (1959)], the difference between the paw volumes 5 hours after oedema provocation and the normal paw volume giving the oedema volume. The analgesic action was determined via pressure pain [Randall-Selitto, see above].

The inhibition of the carrageenan oedema following intramuscular administration of 2-(2-hydroxyethoxy)-ethyl N-(α,α,α-trifluoro-m-tolyl)-anthranilate (formula 11) in viscoleo after various doses in a constant administration volume of 0.03 ml (rat) is as follows:

| Dose mg/kg | Days after injection | Oedema inhibition (%) | Increase in pain (%) |
|---|---|---|---|
| 10.5 | 1 | 64.0 | |
| | 2 | 61.1 | |
| | 3 | 36.6 | |
| | 4 | 41.6 | |
| 15 | 1 | 77.6 | 64.3 (1 hour) |
| | 2 | 72.2 | 75.3 (24 hours) |
| | 3 | 55.5 | 46.6 (48 hours) |
| | 4 | 51.3 | 32.9 (72 hours) |
| 19.5 | 1 | 77.6 | |
| | 2 | 81.3 | |
| | 3 | 61.6 | |
| | 4 | 52.1 | |

In the same model (carrageenan), peroral administration of 2-(2-hydroxyethoxy)-ethyl N-(α,α,α-trifluoro-m-tolyl)-anthranilate leads to powerful oedema inhibition, which, however, corresponds to the control value after about 24 hours [H. Jacobi et al., Arzneimittelforsch. 27, 1328 (1977)].

The oedema inhibition following intramuscular administration of butyl N-(α,α,α-trifluoro-m-tolyl)-anthranilate (formula 13) in viscoleo was 53.8, 46.5, 34.3, 37.1 and 28.8% 1, 2, 3, 4 and, respectively, 5 days after a single intramuscular administration of 15 mg/kg.

The following acids produce the following inhibition after intramuscular administration of 15 mg/kg as an oily solution:

| | % Inhibition after depot acid | |
|---|---|---|
| Days after injection | N—(α,α,α-trifluoro-m-tolyl)anthranilic acid (formula 1) | 2-(α,α,α-trifluoro-m-(toluidino)-nicotinic acid (formula 6) |
| 1 | 53.8 | 57.0 |
| 2 | 46.5 | 35.2 |
| 3 | 34.3 | 35.5 |
| 4 | 37.1 | 11.5 |
| 5 | 26.8 | |

It was possible to determine the biological half-life (HL) of the compound 11 in rats from the inflamed tissue by means of gas chromatography [H.-D. Dell, J. Fielder, H. Jacobi and J. Kolle, Arzneim.-Forsch./-Drug.Res 31, 17–21 (1981)]. The HL from the tissue is about 8.5 hours. In contrast, an HL of 1.29 days is determined for elimination from the tissue (site of administration) following intramuscular administration of 11 in oily solution.

The present invention also includes the use of the depot products in medicine as antiinflammatory or analgesic agents.

In general, it is advisable, both in medicine, to administer the above active compounds according to the invention in total amounts of about 0.1 to about 100 mg/kg, preferably 0.3 to 10 mg/kg, of body weight per injection. However, it may be necessary to deviate from the dosages mentioned, and in particular to do so as a function of the nature and body weight of the subject to be treated and the nature and severity of the disease.

The following examples illustrate injectable oily solutions or suspensions according to the invention, which can be used as depot antiinflammatory agents or depot analgesics, and are particularly preferred compositions:

| | | |
|---|---|---|
| A 1 | 2-2-(Hydroxyethoxy)-ethyl N—(α,α,α-trifluoro-m-tolyl)-anthranilate (formula 11) | 500 g |
| | Viscoleo | to 1,000 g |
| 2 | 2-2-(Hydroxyethoxy)-ethyl N—(α,α,α-trifluoro-m-tolyl)-anthranilate (formula 11) | 500 g |
| | Isopropyl myristate | to 1,000 g |
| 3 | 2-(2-Hydroxyethoxy)-ethyl N—(α,α,α-trifluoro-m-tolyl)-anthranilate (formula 11) | 400 g |
| | Propyl gallate | 10 g |
| | Ethyl oleate | to 1,000 g |
| 4 | 2-(2-Hydroxyethoxy)-ethyl N—(α,α,α-trifluoro-m-tolyl)-anthranilate (formula 11) | 400 g |
| | Miglyol 812 | to 1,000 g |
| B 1 | Butyl N—(α,α,α-trifluoro-m-tolyl)-anthranilate (formula 13) | 500 g |
| | Viscoleo | to 1,000 g |
| B 2 | Ethyl-N—(α,α,α-trifluoro-m-tolyl)-anthranilate (formula 14) | 500 g |
| | Isopropyl myristate | to 1,000 g |
| 3 | Isopropyl-N—(α,α,α-trifluoro-m-tolyl)-anthranilate (formula 15) | 490 g |
| | Propyl gallate | 10 g |
| | Ethyl oleate | to 1,000 g |
| 4 | Butyl-N—(α,α,α-trifluoro-m-tolyl)-anthranilate (formula 13) | 600 g |
| | Miglyol 812 | to 1,000 g |
| C 1 | N—(α,α,α-Trifluoro-m-tolyl)-anthranilic acid (formula 1) | 170 g |
| | Aluminium stearate | 20 g |
| | Miglyol 812 | to 1,000 g |
| 2 | N—(2,3-Xylyl)-anthranilic acid (formula 2) | 170 g |
| | Aluminium stearate | 15 g |
| | Viscoleo | to 1,000 g |
| 3 | 2-(α,α,α-Trifluoro-m-toluidino)-nicotinic acid (formula 6) | 300 g |
| | Propyl gallate | 10 g |
| | Castor oil | to 1,000 g |
| 4 | N—(2,6-Dichloro-m-tolyl)-anthranilic acid (formula 3) | 400 g |
| | Propyl gallate | 10 g |
| | Sesame oil | to 1,000 g |

| | |
|---|---|
| Arachis oil = | oleum arachidis neutralisatum |
| Cottonseed oil = | oleum gossypii neutralisatum |
| Almond oil = | oleum amygdalae neutralisatum |
| Olive oil = | oleum olivae neutralisatum |
| Sesame oil = | oleum sesami neutralisatum |
| Castor oil = | oleum ricini neutralisatum |
| Neat's foot oil = | oleum pedis bovis/equi |
| Neutral oil = | oleum neutrale (for example Miglyol) |
| Maize oil = | oleum maydis neutralisatum |

Miglyol 812 is a caprylic/capric acid triglyceride, compare Fielder, Lexikon der Hilfsstoffe [Encyclopaedia of Auxiliaries], Editro Canter, Aulendorf, 2nd Edition, 1981, page 616.

TABLE 1

| Example | Active compound N—(α,α,α-trifluoro-m-tolyl)-anthranilic acid (1) (mg) | Solution or suspension medium (to 1,000 mg) | Propyl gallate (mg) | Al stearate (mg) | Neutral oil (mg) |
|---|---|---|---|---|---|
| 1 | 300 | Arachis oil | 10 | | |
| 2 | 120 | " | 10 | | |
| 3 | 250 | Cottonseed oil | | | |
| 4 | 100 | " | | 20 | |
| 5 | 250 | Almond oil | | | |
| 6 | 100 | " | | | |
| 7 | 300 | Maize oil | | | |
| 8 | 120 | " | | | |
| 9 | 300 | Olive oil | 10 | | |
| 10 | 120 | " | 10 | | |
| 11 | 250 | Castor oil | 10 | | |
| 12 | 100 | " | 10 | | |
| 13 | 250 | Sesame oil | | | |
| 14 | 100 | " | | | |
| 15 | 300 | Neat's foot oil | | 20 | |
| 16 | 120 | " | | | |
| 17 | 300 | Neutral oil | | 20 | |

TABLE 2

| Example | Active compound N—(2,3-xylyl)-anthranilic acid (2) (mg) | Solution or suspension medium (to 1,000 mg) | Propyl gallate (mg) | Al stearate (mg) | Neutral oil (mg) |
|---|---|---|---|---|---|
| 1 | 300 | Arachis oil | 10 | | |
| 2 | 120 | " | 10 | | |
| 3 | 250 | Cottonseed oil | | | |
| 4 | 100 | " | | 20 | |
| 5 | 250 | Almond oil | | | |
| 6 | 100 | " | | | |
| 7 | 300 | Maize oil | | | |
| 8 | 120 | " | | | |

TABLE 2-continued

| Example | Active compound N—(2,3-xylyl)-anthranilic acid (2) (mg) | Solution or suspension medium (to 1,000 mg) | Propyl gallate (mg) | Al stearate (mg) | Neutral oil (mg) |
|---|---|---|---|---|---|
| 9 | 300 | Olive oil | 10 | | |
| 10 | 120 | " | 10 | | |
| 11 | 250 | Castor oil | 10 | | |
| 12 | 100 | " | 10 | | |
| 13 | 250 | Sesame oil | | | |
| 14 | 100 | " | | | |
| 15 | 300 | Neat's foot oil | | 20 | |
| 16 | 120 | " | | | |
| 17 | 300 | Neutral oil | | 20 | |

TABLE 3

| Example | Active compound N—(2,6-dichloro-m-tolyl)-anthranilic acid (3) (mg) | Solution or suspension medium (to 1,000 mg) | Propyl gallate (mg) | Al stearate (mg) | Neutral oil (mg) |
|---|---|---|---|---|---|
| 1 | 300 | Ethyl oleate | | | |
| 2 | 120 | " | | | |
| 3 | 250 | Isopropyl myristate | | | |
| 4 | 100 | " | | 20 | |
| 5 | 250 | Isopropyl palmitate | | | |
| 6 | 120 | " | | | |
| 7 | 300 | Oleyl oleate | | | |
| 8 | 100 | " | | | |
| 9 | 250 | Benzyl benzoate | | | 300 |
| 10 | 100 | " | | | 400 |
| 11 | 300 | Poppyseed oil | 10 | | |
| 12 | 120 | " | 10 | | |
| 13 | 300 | Viscoleo | | | |
| 14 | 120 | " | | 20 | |

TABLE 4

| Example | Active compound N—(3-chloro-o-tolyl)-anthranilic acid (4) (mg) | Solution or suspension medium (to 1,000 mg) | Propyl gallate (mg) | Al stearate (mg) | Neutral oil (mg) |
|---|---|---|---|---|---|
| 1 | 300 | Arachis oil | 10 | | |
| 2 | 120 | " | 10 | | |
| 3 | 250 | Cottonseed oil | | | |
| 4 | 100 | " | | 20 | |
| 5 | 250 | Almond oil | | | |
| 6 | 100 | " | | | |
| 7 | 300 | Maize oil | | | |
| 8 | 120 | " | | | |
| 9 | 300 | Olive oil | 10 | | |
| 10 | 120 | " | 10 | | |
| 11 | 250 | Castor oil | 10 | | |
| 12 | 100 | " | 10 | | |
| 13 | 250 | Sesame oil | | | |
| 14 | 100 | " | | | |
| 15 | 300 | Neat's foot oil | | 20 | |
| 16 | 120 | " | | | |
| 17 | 300 | Neutral oil | | 20 | |

TABLE 5

| Example | Active compound N—(2,3-dichloro-phenyl)-anthranilic acid (5) (mg) | Solution or suspension medium (to 1,000 mg) | Propyl gallate (mg) | Al stearate (mg) | Neutral oil (mg) |
|---|---|---|---|---|---|
| 1 | 300 | Ethyl oleate | | | |
| 2 | 120 | " | | | |
| 3 | 250 | Isopropyl myristate | | | |
| 4 | 100 | " | | 20 | |
| 5 | 250 | Isopropyl palmitate | | | |
| 6 | 120 | " | | | |
| 7 | 300 | Oleyl oleate | | | |
| 8 | 100 | " | | | |
| 9 | 250 | Benzyl benzoate | | | 300 |
| 10 | 100 | " | | | 400 |
| 11 | 300 | Poppyseed oil | 10 | | |

TABLE 5-continued

| Example | Active compound N—(2,3-dichloro-phenyl)-anthran-ilic acid (5) (mg) | Solution or suspension medium (to 1,000 mg) | Propyl gallate (mg) | Al stearate (mg) | Neutral oil (mg) |
|---|---|---|---|---|---|
| 12 | 120 | " | 10 | | |
| 13 | 300 | Viscoleo | | | |
| 14 | 120 | " | | 20 | |

TABLE 6

| Example | Active compound 2-(α,α,α-tri-fluoro-m-tolui-dine)-nicotinic acid (6) (mg) | Solution or suspension medium (to 1,000 mg) | Propyl gallate (mg) | Al stearate (mg) | Neutral oil (mg) |
|---|---|---|---|---|---|
| 1 | 300 | Arachis oil | 10 | | |
| 2 | 120 | " | 10 | | |
| 3 | 250 | Cottonseed oil | | | |
| 4 | 100 | " | | 20 | |
| 5 | 250 | Almond oil | | | |
| 6 | 100 | " | | | |
| 7 | 300 | Maize oil | | | |
| 8 | 120 | " | | | |
| 9 | 300 | Olive oil | 10 | | |
| 10 | 120 | " | 10 | | |
| 11 | 250 | Castor oil | 10 | | |
| 12 | 100 | " | 10 | | |
| 13 | 250 | Sesame oil | | | |
| 14 | 100 | " | | | |
| 15 | 300 | Neat's foot oil | | 20 | |
| 16 | 120 | " | | | |
| 17 | 300 | Neutral oil | | 20 | |

TABLE 7

| Example | Active compound 2-(2,3-xylidino)-nicotinic acid (7) (mg) | Solution or suspension medium (to 1,000 mg) | Propyl gallate (mg) | Al stearate (mg) | Neutral oil (mg) |
|---|---|---|---|---|---|
| 1 | 300 | Ethyl oleate | | | |
| 2 | 120 | " | | | |
| 3 | 250 | Isopropyl myristate | | | |
| 4 | 100 | " | | 20 | |
| 5 | 250 | Isopropyl palmitate | | | |
| 6 | 120 | " | | | |
| 7 | 300 | Oleyl oleate | | | |
| 8 | 100 | " | | | |
| 9 | 250 | Benzyl benzoate | | | 300 |
| 10 | 100 | " | | | 400 |
| 11 | 300 | Poppyseed oil | 10 | | |
| 12 | 120 | " | 10 | | |
| 13 | 300 | Viscoleo | | | |
| 14 | 120 | " | | 20 | |

TABLE 8

| Example | Active compound 2-(2-methyl-3-trifluoromethyl-anilino)-nicotinic acid (8) (mg) | Solution or suspension medium (to 1,000 mg) | Propyl gallate (mg) | Al stearate (mg) | Neutral oil (mg) |
|---|---|---|---|---|---|
| 1 | 300 | Arachis oil | 10 | | |
| 2 | 120 | " | 10 | | |
| 3 | 250 | Cottonseed oil | | | |
| 4 | 100 | " | | 20 | |
| 5 | 250 | Almond oil | | | |
| 6 | 100 | " | | | |
| 7 | 300 | Maize oil | | | |
| 8 | 120 | " | | | |
| 9 | 300 | Olive oil | 10 | | |
| 10 | 120 | " | 10 | | |
| 11 | 250 | Castor oil | 10 | | |
| 12 | 100 | " | 10 | | |
| 13 | 250 | Sesame oil | | | |
| 14 | 100 | " | | | |
| 15 | 300 | Neat's foot oil | | 20 | |
| 16 | 120 | " | | | |

TABLE 8-continued

| Example | Active compound 2-(2-methyl-3-trifluoromethyl-anilino)-nicotinic acid (8) (mg) | Solution or suspension medium (to 1,000 mg) | Propyl gallate (mg) | Al stearate (mg) | Neutral oil (mg) |
|---|---|---|---|---|---|
| 17 | 300 | Neutral oil | | 20 | |

TABLE 9

| Example | Active compound 2-(3-chloro-o-toluidine)-nicotinic acid (9) (mg) | Solution or suspension medium (to 1,000 mg) | Propyl gallate (mg) | Al stearate (mg) | Neutral oil (mg) |
|---|---|---|---|---|---|
| 1 | 300 | Ethyl oleate | | | |
| 2 | 120 | " | | | |
| 3 | 250 | Isopropyl myristate | | | |
| 4 | 100 | " | | 20 | |
| 5 | 250 | Isopropyl palmitate | | | |
| 6 | 120 | " | | | |
| 7 | 300 | Oleyl oleate | | | |
| 8 | 100 | " | | | |
| 9 | 250 | Benzyl benzoate | | | 300 |
| 10 | 100 | " | | | 400 |
| 11 | 300 | Poppyseed oil | 10 | | |
| 12 | 120 | " | 10 | | |
| 13 | 300 | Viscoleo | | | |
| 14 | 120 | " | | 20 | |

TABLE 10

| Example | Active compound 2-(2,6-xylidino)-nicotinic acid (10) (mg) | Suspension medium (to 1,000 mg) | Propyl gallate (mg) | Al stearate (mg) | Neutral oil (mg) |
|---|---|---|---|---|---|
| 1 | 300 | Arachis oil | 10 | | |
| 2 | 120 | " | 10 | | |
| 3 | 250 | Cottonseed oil | | | |
| 4 | 100 | " | | 20 | |
| 5 | 250 | Almond oil | | | |
| 6 | 100 | " | | | |
| 7 | 300 | Maize oil | | | |
| 8 | 120 | " | | | |
| 9 | 300 | Olive oil | 10 | | |
| 10 | 120 | " | 10 | | |
| 11 | 250 | Castor oil | 10 | | |
| 12 | 100 | " | 10 | | |
| 13 | 250 | Sesame oil | | | |
| 14 | 100 | " | | | |
| 15 | 300 | Neat's foot oil | | 20 | |
| 16 | 120 | " | | | |
| 17 | 300 | Neutral oil | | 20 | |

TABLE 11

| Example | Active compound 2-(2-hydroxy-ethoxy)-ethyl N—(α,α,α-trifluoro-m-tolyl)-anthranilate (11) (mg) | Solution or suspension medium (to 1,000 mg) | Propyl gallate (mg) | Al stearate (mg) | Neutral oil (mg) |
|---|---|---|---|---|---|
| 1 | 450 | Arachis oil | 10 | | |
| 2 | 250 | " | 10 | | |
| 3 | 500 | Cottonseed oil | | 20 | |
| 4 | 250 | " | | | |
| 5 | 480 | Almond oil | | | |
| 6 | 200 | " | | | |
| 7 | 500 | Maize oil | | | |
| 8 | 250 | " | | | |
| 9 | 400 | Olive oil | 10 | | |
| 10 | 250 | " | 10 | | |
| 11 | 400 | Castor oil | 10 | | |
| 12 | 200 | " | 10 | | |
| 13 | 450 | Sesame oil | | | |
| 14 | 220 | " | | | |
| 15 | 500 | Neat's foot oil | | | |
| 16 | 250 | " | | 20 | |

TABLE 11-continued

| Example | Active compound 2-(2-hydroxy-ethoxy)-ethyl N—(α,α,α-trifluoro-m-tolyl)-anthranilate (11) (mg) | Solution or suspension medium (to 1,000 mg) | Propyl gallate (mg) | Al stearate (mg) | Neutral oil (mg) |
|---|---|---|---|---|---|
| 17 | 550 | Neutral oil | | | |
| 18 | 300 | " | | 20 | |
| 19 | 500 | Ethyl oleate | | | |
| 20 | 250 | " | | | |
| 21 | 550 | Isopropyl myristate | | | |
| 22 | 300 | " | | 20 | |
| 23 | 550 | Isopropyl palmitate | | | |
| 24 | 300 | " | | | |
| 25 | 500 | Oleyl oleate | | | |
| 26 | 250 | " | | | |
| 27 | 450 | Benzyl benzoate | | | 250 |
| 28 | 200 | " | | | 500 |
| 29 | 450 | Poppyseed oil | 10 | | |
| 30 | 250 | " | 10 | | |
| 31 | 500 | Viscoleo | | | |
| 32 | 250 | " | | 20 | |

TABLE 12

| Example | Active compound ethoxymethyl N—(2,6-dichloro-m-tolyl)-anthranilate (12) (mg) | Solution or suspension medium (to 1,000 mg) | Propyl gallate (mg) | Al stearate (mg) | Neutral oil (mg) |
|---|---|---|---|---|---|
| 1 | 450 | Arachis oil | 10 | | |
| 2 | 250 | " | 10 | | |
| 3 | 500 | Cottonseed oil | | 20 | |
| 4 | 250 | " | | | |
| 5 | 480 | Almond oil | | | |
| 6 | 200 | " | | | |
| 7 | 500 | Maize oil | | | |
| 8 | 250 | " | | | |
| 9 | 400 | Olive oil | 10 | | |
| 10 | 250 | " | 10 | | |
| 11 | 400 | Castor oil | 10 | | |
| 12 | 200 | " | 10 | | |
| 13 | 450 | Sesame oil | | | |
| 14 | 220 | " | | | |
| 15 | 500 | Neat's foot oil | | | |
| 16 | 250 | " | | 20 | |
| 17 | 550 | Neutral oil | | | |
| 18 | 300 | " | | 20 | |
| 19 | 500 | Ethyl oleate | | | |
| 20 | 250 | " | | | |
| 21 | 550 | Isopropyl myristate | | | |
| 22 | 300 | " | | 20 | |
| 23 | 550 | Isopropyl palmitate | | | |
| 24 | 300 | " | | | |
| 25 | 500 | Oleyl oleate | | | |
| 26 | 250 | " | | | |
| 27 | 450 | Benzyl benzoate | | | 250 |
| 28 | 200 | " | | | 500 |
| 29 | 450 | Poppyseed oil | 10 | | |
| 30 | 250 | " | 10 | | |
| 31 | 500 | Viscoleo | | | |
| 32 | 250 | " | | 20 | |

TABLE 13

| Example | Active compound butyl-N—(α,α,α-trifluoro-m-tolyl)-anthranilate (13) (mg) | Solution or suspension medium (to 1,000 mg) | Propyl gallate (mg) | Al stearate (mg) | Neutral oil (mg) |
|---|---|---|---|---|---|
| 1 | 450 | Arachis oil | 10 | | |
| 2 | 250 | " | 10 | | |
| 3 | 500 | Cottonseed oil | | 20 | |
| 4 | 250 | " | | | |
| 5 | 480 | Almond oil | | | |
| 6 | 200 | " | | | |
| 7 | 500 | Maize oil | | | |
| 8 | 250 | " | | | |
| 9 | 400 | Olive oil | 10 | | |

TABLE 13-continued

| Example | Active compound butyl-N—(α,α,α-trifluoro-m-tolyl)-anthranilate (13) (mg) | Solution or suspension medium (to 1,000 mg) | Propyl gallate (mg) | Al stearate (mg) | Neutral oil (mg) |
|---|---|---|---|---|---|
| 10 | 250 | " | 10 | | |
| 11 | 400 | Castor oil | 10 | | |
| 12 | 200 | " | 10 | | |
| 13 | 450 | Sesame oil | | | |
| 14 | 220 | " | | | |

TABLE 14

| Example | Active compound ethyl-N—(α,α,α-trifluoro-m-tolyl)-anthranilate (14a) (mg) | Solution or suspension medium (to, 1,000 mg) | Propyl gallate (mg) | Al stearate (mg) | Neutral oil (mg) |
|---|---|---|---|---|---|
| 1 | 500 | Neat's foot oil | | | |
| 2 | 250 | " | | 20 | — |
| 3 | 550 | Neutral oil | | | |
| 4 | 300 | " | | 20 | |
| 5 | 500 | Ethyl oleate | | | |
| 6 | 250 | " | | | |
| 7 | 550 | Isopropyl myristate | | | |
| 8 | 300 | " | | 20 | |
| 9 | 550 | Isopropyl palmitate | | | |
| 10 | 300 | " | | | |
| 11 | 500 | Oleyl oleate | | | |
| 12 | 250 | " | | | |
| 13 | 450 | Benzyl benzoate | | | |
| 14 | 200 | " | | | |
| 15 | 450 | Poppyseed oil | 10 | | |
| 16 | 250 | " | 10 | | |
| 17 | 500 | Viscoleo | | | |
| 18 | 250 | " | | 20 | |

TABLE 15

| Example | Active compound isopropyl-N—(α,α,α-trifluoro-m-tolyl)-anthranilate (14b) (mg) | Solution or suspension medium (to 1,000 mg) | Propyl gallate (mg) | Al stearate (mg) | Neutral oil (mg) |
|---|---|---|---|---|---|
| 1 | 500 | Neat's foot oil | | | |
| 2 | 250 | " | | 20 | |
| 3 | 550 | Neutral oil | | | |
| 4 | 300 | " | | 20 | |
| 5 | 500 | Ethyl oleate | | | |
| 6 | 250 | " | | | |
| 7 | 550 | Isopropyl myristate | | | |
| 8 | 300 | " | | 20 | |
| 9 | 550 | Isopropyl palmitate | | | |
| 10 | 300 | " | | | |
| 11 | 500 | Oleyl oleate | | | |
| 12 | 250 | " | | | |
| 13 | 450 | Benzyl benzoate | | | |
| 14 | 200 | " | | | |
| 15 | 450 | Poppyseed oil | 10 | | |
| 16 | 250 | " | 10 | | |
| 17 | 500 | Viscoleo | | | |
| 18 | 250 | " | | 20 | |

What is claimed is:

1. A depot agent for intramuscular use containing 3–80% by weight of a compound of the formula (I)

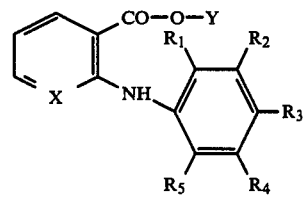

in which $R_1$–$R_5$ represents hydrogen, halogen, alkyl with 1 to 4 C atoms or trihalogenoalkyl, X represents a CH group and Y represents hydrogen, metal ions, alkyl with 1–6 C atoms, alkoxy, alkoxyalkyl, hydroxyalkyl, hydroxyalkoxyalkyl or trihalogenoalkyl, the number of C atoms in each case being between 1 and 6 and to be straight-chain or branched and a suspension medium containing one or more suspension agents selected from the group consisting of: viscoleo, isopropyl myristate, ethyl oleate, castor oil, sesame oil, arachis oil, cottonseed oil, almond oil, olive oil, neat's foot oil, neutral oil and maize oil.

2. A depot agent for intramuscular use containing a compound of the formula (I) according to claim 1, in which $R_3$ and $R_4$ represents hydrogen, $R_1$, $R_2$ and $R_5$ represents methyl, trifluoromethyl or chlorine, X represents a CH group and Y represents hydrogen, metal ions, alkyl with 1 to 4 C atoms or by trihalogeno alkyl and a suspension medium of claim 1.

3. A depot agent for intramuscular use containing a compound of the formula (I) according to claim 1, in which:

$R_3$ and $R_4$ represents hydrogen, $R_1$, $R_2$ and $R_5$ represents methyl, trifluoromethyl or chlorine, X represents a CH group and Y represents hydrogen, a metal ion, alkyl with 1 to 4 C atoms or by substituted alkyl, and a suspension medium of claim 1.

4. A depot agent for intramuscular use containing the compound of the formula (I) according to claim 1, which is 2-(2-hydroxyethoxy)-ethyl N-($\alpha,\alpha,\alpha$-trifluoro-m-toluene)-anthranilate.

5. A depot agent for intramuscular use containing the compound of the formula (I) according to claim 1, which is ethoxymethyl N-(2,6-dichloro-m-tolyl)-anthranilate.

6. A depot agent for intramuscular use containing the compound of the formula (I) according to claim 1, which is butyl-N-($\alpha,\alpha,\alpha$-trifluoro-m-tolyl)-anthranilate.

7. A depot agent for intramuscular use containing the compound of the formula (I) according to claim 1, which is ethyl N-($\alpha,\alpha,\alpha$-trifluoro-m-tolyl)-anthranilate.

8. A depot agent for intramuscular use containing the compound of the formula (I) according to claim 1, which is isopropyl N-($\alpha,\alpha,\alpha$-trifluoro-m-tolyl)-anthranilate.

9. A depot agent for intramuscular use containing a suspension agent and at least one compound from the groups: N-($\alpha,\alpha,\alpha$-trifluoro-m-tolyl)-anthranilic acid (1), N-(2,3-xylyl)-anthranilic acid (2), N-(2,6-dichloro-m-tolyl)-anthranilic acid (3), N-(3-chloro-o-tolyl)-anthranilic acid (4), N-(2,3-dichloro-phenyl)-anthranilic acid (5), N-($\alpha,\alpha,\alpha$-trifluoro-m-toluidine nicotinic acid (6), 2-(2,3-xylidino)-nicotinic acid (7), 2-(2-methyl-3-trifluoromethylanilino)-nicotinic acid (8), 2-(3-chloro-o-toluidine)-nicotinic acid (9), 2-(2,6-xylidino)-nicotinic acid (10), 2-(2-hydroxyethoxy)-ethyl N-($\alpha,\alpha,\alpha$-trifluoro-m-tolyl)-anthranilate (11), ethoxymethyl N-(2,6-dichloro-o-tolyl)-anthranilate (12), butyl(-N-$\alpha,\alpha,\alpha$-trifluoro-m-tolyl)-anthranilate (13), ethyl-N-($\alpha,\alpha,\alpha$-trifluoro-m-tolyl)-anthranilate (14) and isopropyl-N-($\alpha,\alpha,\alpha$-trifluoro-m-tolyl)-anthranilate (15).

10. A depot agent according to claim 1, characterised in that it contains one or more suspension agents from the group: viscoleo, isopropyl myristate, ethyl oleate and neutral oil.

11. A depot agent according to claim 1, characterised in that it contains a compound of the formula (I) according to any of claims 1, 2, 3 or 4 in an amount of 10 to 75% by weight, and a suspension agent selected from viscoleo, isopropyl myristate, ethyl oleate, castor oil, sesame oil, arachis oil, cottonseed oil, almond oil, olive oil, neat's foot oil, neutral oil and maize oil in an amount of 5 to 90% by weight, preferably 20 to 80% by weight.

* * * * *

UNITED STATES PATENT AND TRADEMARK OFFICE
CERTIFICATE OF CORRECTION

PATENT NO. : 4,594,357
DATED : June 10, 1986
INVENTOR(S) : Hans-Dieter Dell, et al.

It is certified that error appears in the above-identified patent and that said Letters Patent is hereby corrected as shown below:

Col. 6, line 1 — Before "5" delete "or" and substitute --of--

Col. 6, line 65 and Col. 8, line 33 — Correct spelling of "Fiedler"

Col. 18, Table 14 — Delete "—" under last column entitled "Neutral Oil (mg)"

Signed and Sealed this

Eighteenth Day of November, 1986

Attest:

DONALD J. QUIGG

Attesting Officer

Commissioner of Patents and Trademarks